United States Patent [19]

Bierman et al.

[11] Patent Number: 5,290,248
[45] Date of Patent: Mar. 1, 1994

[54] SIDEPORT CONNECTOR FOR CATHERIZATION SYSTEM

[75] Inventors: Steven F. Bierman, 143 Eighth St., Del Mar, Calif. 92014; David C. Howson, Denver, Colo.

[73] Assignee: Steven F. Bierman, Del Mar, Calif.

[21] Appl. No.: 892,593

[22] Filed: May 28, 1992

Related U.S. Application Data

[63] Continuation of Ser. No. 695,554, May 3, 1991, abandoned, which is a continuation-in-part of Ser. No. 518,964, May 4, 1990, Pat. No. 5,192,273, which is a continuation-in-part of Ser. No. 384,326, Jul. 24, 1989.

[51] Int. Cl.$^5$ .............................. A61M 5/32
[52] U.S. Cl. .................................... 604/174
[58] Field of Search ............... 604/905, 174, 414, 415, 604/244, 256, 263, 284, 192

[56] References Cited

U.S. PATENT DOCUMENTS

| | | |
|---|---|---|
| 747,360 | 12/1903 | Barry . |
| 2,525,398 | 10/1950 | Collins . |
| 2,533,961 | 12/1950 | Rouseau et al. . |
| 3,064,648 | 11/1962 | Bujan . |
| 3,167,072 | 1/1965 | Stone et al. . |
| 3,245,567 | 4/1966 | Knight ............... 604/263 X |
| 3,394,954 | 7/1968 | Sarns . |
| 3,686,896 | 8/1972 | Rutter . |
| 3,766,915 | 10/1973 | Rychlik . |
| 3,900,026 | 8/1975 | Wagner . |
| 3,906,946 | 9/1975 | Nordstrom . |
| 3,920,001 | 11/1975 | Edwards . |
| 3,973,565 | 8/1976 | Steer . |
| 4,037,599 | 7/1977 | Raulerson . |
| 4,082,094 | 4/1978 | Dailey . |
| 4,084,911 | 4/1978 | DeWitt . |
| 4,099,744 | 7/1978 | Kutnyak et al. . |
| 4,114,618 | 9/1978 | Vargas . |
| 4,116,196 | 9/1978 | Kaplan et al. . |
| 4,123,091 | 10/1978 | Cosentino et al. . |
| 4,129,128 | 12/1978 | McFarlane . |
| 4,133,312 | 1/1979 | Burd . |
| 4,161,177 | 7/1979 | Fuchs . |
| 4,224,937 | 9/1980 | Gordon . |
| 4,250,880 | 2/1981 | Gordon . |
| 4,316,461 | 2/1982 | Marais et al. . |
| 4,326,519 | 4/1982 | D'Alo et al. . |
| 4,362,156 | 12/1982 | Feller, Jr. et al. . |
| 4,392,853 | 7/1983 | Muto . |
| 4,405,163 | 9/1983 | Voges et al. ............... 604/905 X |
| 4,449,975 | 5/1984 | Perry . |
| 4,474,559 | 10/1984 | Steiger . |
| 4,516,968 | 5/1985 | Marshall et al. . |
| 4,585,435 | 4/1986 | Vaillancourt . |
| 4,711,636 | 12/1987 | Bierman . |
| 4,752,292 | 6/1988 | Lopez et al. ............... 604/244 |
| 4,792,163 | 12/1988 | Kulle . |
| 4,834,716 | 5/1989 | Ogle II . |
| 4,838,858 | 6/1989 | Wortham et al. . |
| 4,863,432 | 9/1989 | Kvalo . |
| 4,880,412 | 11/1989 | Weiss . |
| 4,966,582 | 10/1990 | Sit et al. . |
| 4,981,469 | 1/1991 | Whitehouse et al. . |
| 4,997,421 | 3/1991 | Palsrok et al. . |

FOREIGN PATENT DOCUMENTS

| | | |
|---|---|---|
| 2341297 | 4/1975 | European Pat. Off. . |
| 0114677 | 1/1984 | European Pat. Off. . |
| 114677 | 8/1984 | European Pat. Off. . |
| 169704 | 1/1986 | European Pat. Off. . |
| 0367549 | 9/1990 | European Pat. Off. . |
| 0263789 | 9/1986 | Fed. Rep. of Germany . |
| 9005559 | 5/1990 | PCT Int'l Appl. . |
| 9116939 | 11/1991 | PCT Int'l Appl. . |
| 2063679 | 6/1981 | United Kingdom . |
| 2086466 | 12/1982 | United Kingdom . |

*Primary Examiner*—Gene Mancene
*Assistant Examiner*—Jeffrey A. Smith
*Attorney, Agent, or Firm*—Knobbe, Martens, Olson & Bear

[57] ABSTRACT

A sideport connector for an IV catheterization system is disclosed in which a secure connection can be maintained with standard Y-shaped sideport connectors, such as a septum-type connector. The connector of the present invention comprises a clip having a collar which slidably and, optionally, rotatably engages the septum in order to prevent accidental disengagement. The clip is prevented from disengaging motion by, preferably, a ratchet-pawl mechanism. In another embodiment, the clip can be mounted on the branch of the Y-shaped sideport. The connector also comprises a needle shield or, optionally, a cap to prevent self-injection and contamination.

19 Claims, 3 Drawing Sheets

TO PATIENT

SIDEPORT CONNECTOR FOR CATHERIZATION SYSTEM

RELATED APPLICATION

This is a continuation of application Ser. No. 07/695,554, filed May 3, 1991, now abandoned, which is a continuation-in-part of co-pending U.S. patent application Ser. No. 518,964, filed May 4, 1990, now U.S. Pat. No. 5,192,273, which is a continuation-in-part application of Ser. No. 384,326, filed Jul. 24, 1989, now abandoned.

BACKGROUND OF THE INVENTION

The present invention relates to a sideport connector for use in conjunction with standard catheterization systems and components, and, more particularly, to a connection system which provides secure connections at such sideport locations with respect to septum-type connectors.

It is very common in the treatment of hospitalized and home healthcare patients to utilize intravenous ("IV") catheters to introduce certain fluids and medications directly into the bloodstream of the patient. Such procedures are becoming more common outside of the hospital as the high cost of hospital medical care has brought about the advent of neighborhood outpatient clinics and home healthcare.

In IV catheterization, a supply fluid is maintained in a container which is located at a height higher than the patient. The catheter tubing flows from the supply container to the location of introduction (or "injection site") into the patient where it is attached to a catheter extending into the vein of the patient. This location is typically the back of the patient's hand or a vein on the inside of the arm. Typically, a needle or other stylet is first introduced to the cannula portion of the catheter and then into the skin of the patient at the desired location. The needle is then removed, leaving the cannula in place in the vein. The fluid then flows directly into the blood vessel of the patient by gravity and/or by the pressure generated by the head of the fluid above the height of the patient.

In common practice, a single fluid supply line is established by means of such IV catheterization. However, it is frequently desirable to introduce a second fluid into the bloodstream of the patient or to administer to the patient smaller doses of medication by means of manual injection. In order to avoid a second IV wound, the established IV line is usually provided with a Y-shaped connector, frequently termed a "sideport." For example, a second fluid can be merged with the first fluid by connecting the tubing of the second container at the sideport so that the two fluids mix together as they are introduced into the bloodstream of the patient through the single, downstream IV tubing. Likewise, manual injections can be administered at the sideport location in order to avoid the pain and discomfort of an injection directly into the patient.

The connection at the sideport can be one of a variety of standard type connectors such as a luer-type or septum cap connector. One advantage of the septum cap is that it permits both types of sideport connections, e.g., a second IV fluid or manual injections. The septum cap connector (also commonly referred to as a "heparin lock" or "buff cap") is comprised of a cylindrical tube which extends from a Y-shaped connector in the main IV line. The open end of the tube is provided with a rubber septum cap which is stretched over the tube or inserted within it to completely cover the opening. A beveled needle, which can either be attached to the end of an IV line or to a manual injection device, is inserted through the rubber material of the septum and into the lumen on the other side of the septum in order to permit the confluence of fluid into the main IV line. Once the needle is withdrawn, the rubber material of the septum cap is self-sealing in that the puncture area is automatically closed. Thus, the septum cap advantageously provides rapid access for injections or secondary IV attachments. The top surface of the septum can be easily cleaned and sterilized.

Although this type of connection has several advantages, it also presents a few problems. The mechanical security of the connection is poor. The needle simply is securely retained by the thin rubber sheet forming the septum cap. Patients receiving this type of IV therapy are often ambulatory thus increasing the degree of movement and motion of the IV tubing and the risk of accidental disconnection. Furthermore, long-term infusion is becoming more prevalent, again increasing the risk of disconnection. There is also a significant risk of accidental self-injection by the needle and there is no means to prevent contamination of the connection at the sideport.

Accordingly, nurses and others who must utilize this type of IV therapy typically attempt to secure the connection by means of surgical tape. However, this method has been shown to be less than desirable because it is time consuming and still does not prevent contamination. Furthermore, existing products which have attempted to solve this problem have done so by providing two separate customized connectors, one at the sideport and one on the IV tubing, which must be joined together. In other words, such previous products are not compatible with standard septum or luer connectors, but are only compatible with connectors manufactured by the same company. This is very inconvenient to the user and also increases the cost of such standard IV therapy. Other connectors are available which attach to both the sideport and the distal end of the IV tubing; however, they have proven to be awkward and cumbersome and not much of an improvement over the use of surgical tape.

SUMMARY OF THE INVENTION

The present invention provides a sideport connector with a mechanism for securely and compatibly engaging standard connectors, such as septum cap connectors. The invention is comprised of an adaptor having a tubular body mounted on the distal end of standard IV tubing. Extending distally from the adaptor body is a standard IV needle for insertion into the septum cap. Mounted on the adaptor body is an arm including a housing through which a clip is slidably engaged. The clip includes a forward latch or collar portion which, upon connection at the sideport, engages the septum cap about the circumference thereof to securely maintain the connection.

The clip is provided with a ratcheted surface which is engaged by a pawl mounted in the housing of the adaptor body. The ratchet-pawl assembly permits the clip to slidably engage the septum cap in order to tighten and secure the sideport connection, but prevents movement in the opposite direction. The latch or collar end of the clip is configured so as to accommodate a wide variety of dimensions and configurations of septum-type connectors as well as other standard types of connectors.

The adaptor body is also provided with a partially cylindrical shield extending distally from the body and partially surrounding the needle so as to prevent accidental self-injection. The shield also inhibits contamination at the connection site. In another embodiment of the invention, the needle of the adaptor, when disengaged from the septum cap, can be protected by a needle cap which completely surrounds the needle. The needle cap is provided with a finger grip to advantageously facilitate capping and decapping.

In one embodiment, the connector of the present invention is mounted on the distal end of the IV tubing. In another embodiment, the clip assembly is mounted on the Y-shaped sideport connector.

Thus, the present invention provides a simple and inexpensive solution to the problems arising with relation to IV connections at sideports. In particular, the connector of the present invention is compatible with standard connections, and the expense and inconvenience of matching, two-piece custom connectors is avoided.

DETAILED DESCRIPTION OF THE INVENTION

Figure 1:
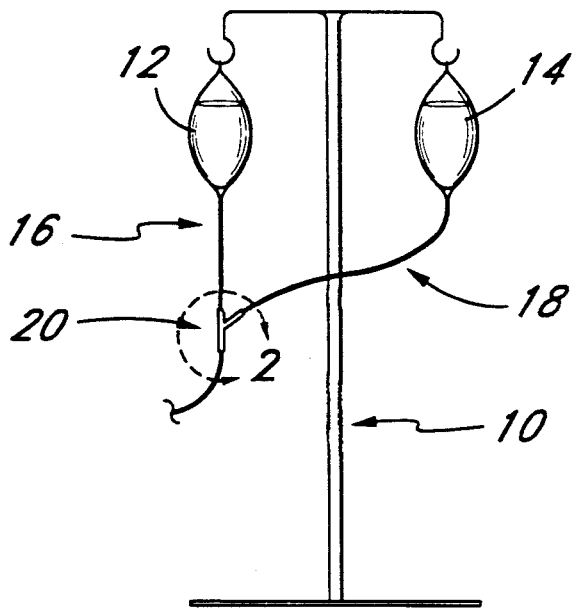
FIG. 1 is a schematic view of a typical catheterization installation illustrating both a primary IV line and a merging secondary IV line joined at a sideport connection.

FIG. 1 illustrates, in a very schematic manner, a standard catheterization system, including a support stand 10, a primary fluid container 12 and a secondary fluid container 14. The primary IV line 16 or tubing extends to an injection site at the patient (not shown). The secondary IV line 18 joins the primary line 16 at a sideport connection 20, as illustrated in more detail in FIG. 2.

Figure 2:
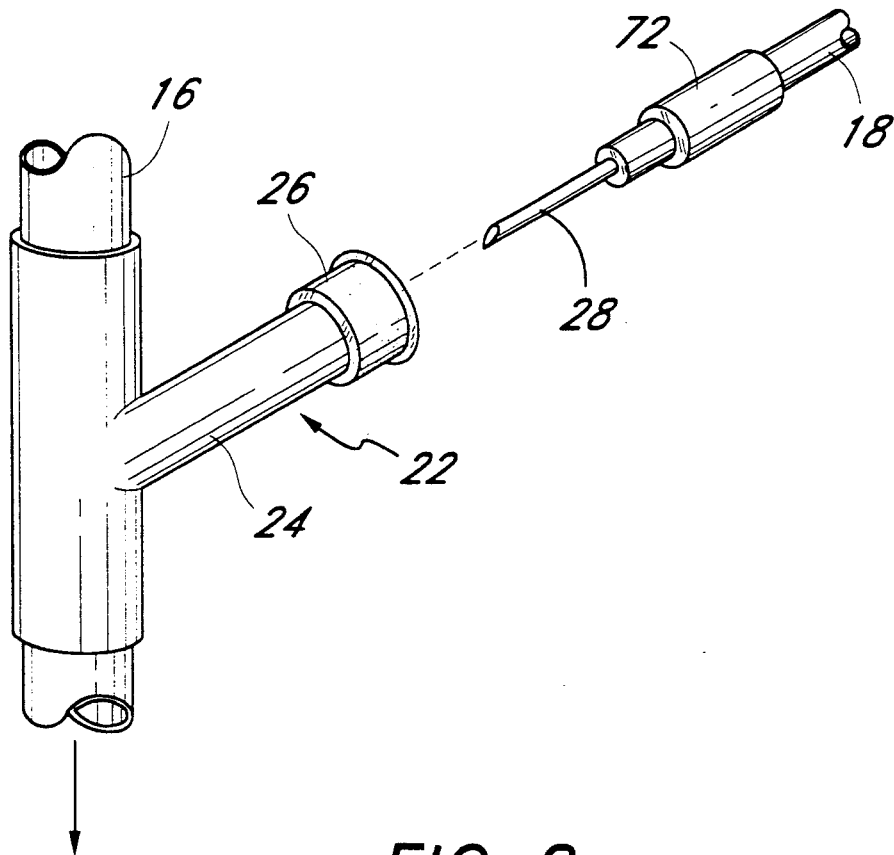
FIG. 2 is a close-up perspective view of a standard sideport connection.

Referring to FIG. 2, there is shown a standard Y-shaped sideport connector 22 having a branch line 24 to receive the secondary fluid line 18. In the case of FIG. 2, the sideport 22 is provided with a septum cap 26 which is comprised of a rubber cap stretched tightly over the end of the tubular branch 24. Although the present invention is illustrated in connection with a septum connector, its principles apply equally to other types of connectors. The secondary IV line 18 is provided with a beveled needle 28 at its distal end which is then inserted through the septum cap 26 so that the secondary fluid converges with the primary fluid and subsequently flows into the bloodstream of the patient. Obviously, under modern IV conditions, the security of this connection is extremely doubtful.

Figure 3:
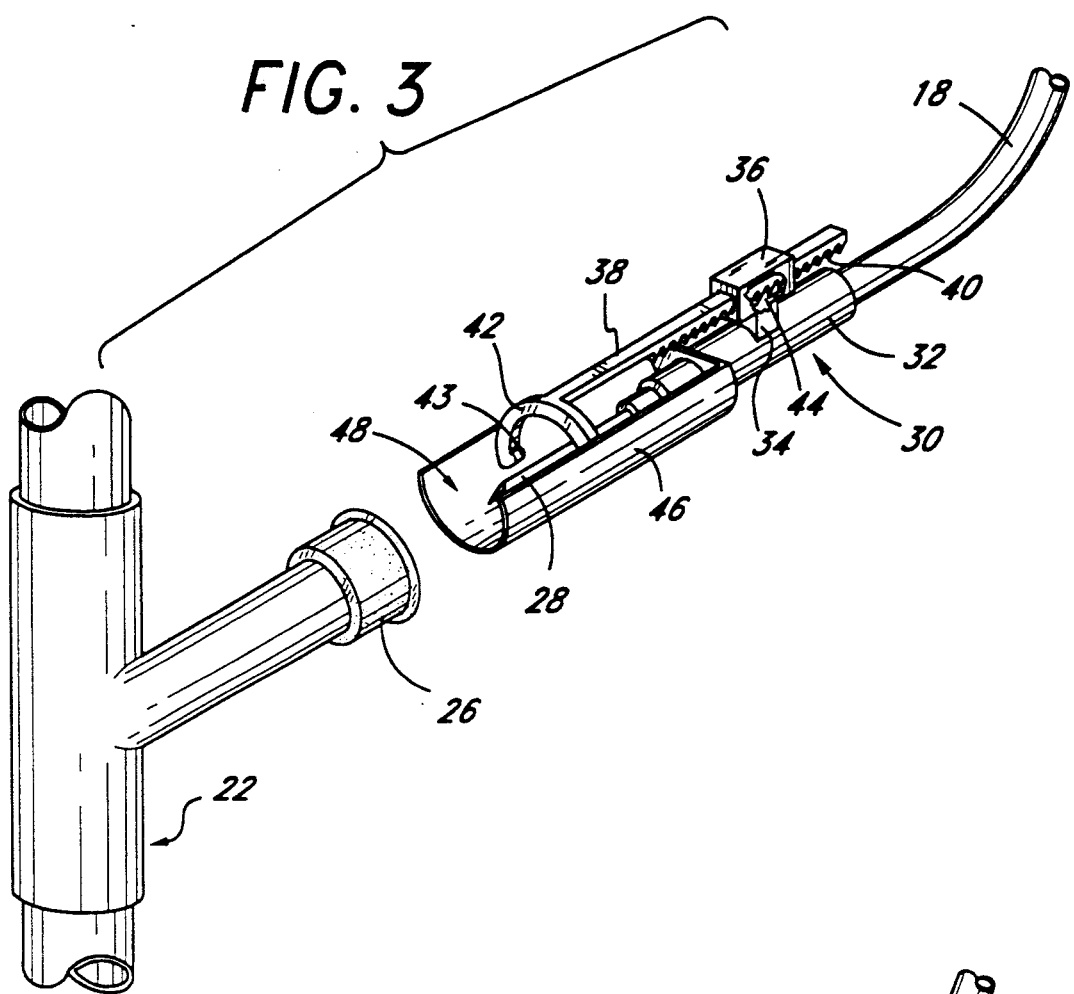
FIG. 3 is a perspective view of the connector of the present invention as it is about to be engaged with a septum cap connector.
Figure 4:
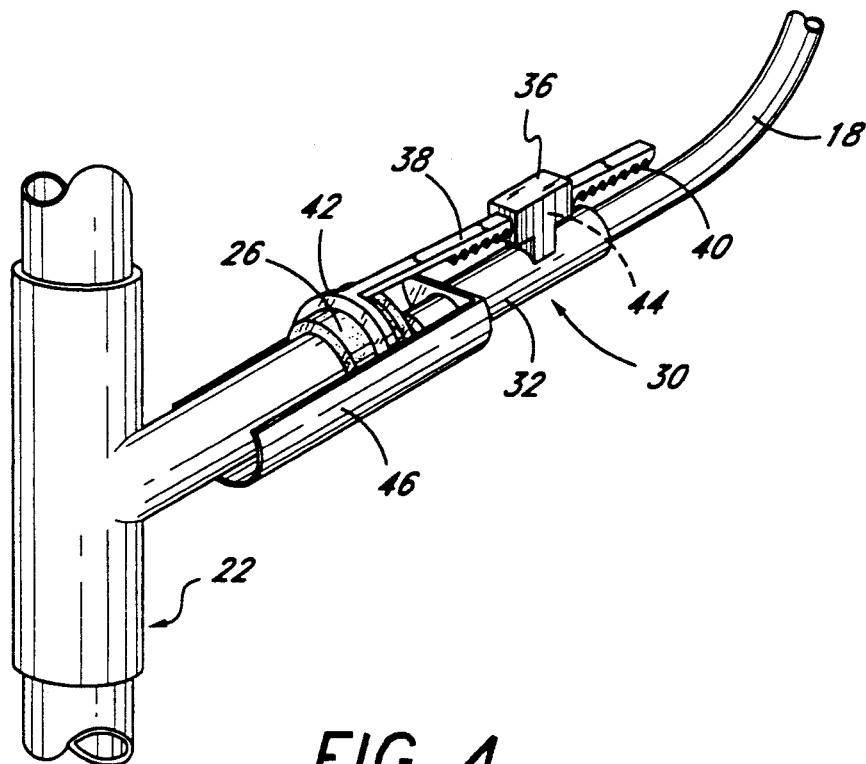
FIG. 4 illustrates the connector of the present invention after the sideport connection is completed.

The sideport connector of the present invention, as illustrated in FIGS. 3 and 4, provides a secure means of sideport connection which is compatible with standard connectors, including the type illustrated in FIG. 2. Referring, then to FIG. 3, there is shown an adaptor 30 of the present invention mounted on the distal end of a standard IV tubing 18. The adaptor 30 is comprised of a tubular body 32 having a standard IV needle 28 extending distally therefrom. Extending approximately transversely from the body is an arm 34 which terminates in a pawl housing 36. Extending through the pawl housing 36 is a slidable clip 38 having a surface 40 which is beveled or ratcheted as shown. The clip terminates in a U-shaped or horseshoe-shaped collar 42 for secure engagement with the septum cap 26, as explained in more detail below in connection with FIG. 4.

The clip 38 is initially assembled in the pawl housing 36 in an extended position with respect to the body 32. A standard pawl 44 is mounted in the pawl housing 36 so as to engage the ratcheted surface 40 of the clip 38. The clip 38 is mounted for slidable movement in the pawl housing but only in a proximal direction, the pawl 44 preventing movement in the distal direction. The adaptor body 32 is provided with a needle shield 46 which partially, substantially surrounds the needle 28, as shown in FIG. 3. This shield 46 is mounted on the distal end of the body 32 and is provided with an upper opening 48 along one longitudinal surface thereof to prevent interference with the collar 42 of the clip. This shield 46 extends distally so as to be slightly forward of the tip of the needle 28, thus serving to prevent accidental self-injection while the sideport connection is being completed. The shield 46 substantially surrounds the needle 28 in the range of about 160°–220°; although, other shield configurations are within the scope of the present invention. This shield also serves to inhibit contamination at the sideport connection site, as illustrated in more detail in FIG. 4.

Referring to FIG. 4, there is shown the connector 30 of the present invention after the sideport connection of FIG. 3 is completed. Thus, it can be seen that the shield 46 substantially surrounds the septum cap 26 in order to prevent contamination. However, it should be pointed out that the present invention can be utilized with or without the shield 46. In addition, the collar 42 on the clip 38 is securely engaging the septum cap 26 so as to prevent accidental disconnection. The collar is maintained in place by the interengagement of the ratcheted surface 40 on the clip and the pawl 44. Thus, the present invention advantageously permits a secure connection to a standard septum sideport.

In operation, referring again to FIGS. 3 and 4, the needle 28 of the IV tubing is inserted into the septum cap 26 in order to make the fluid connection. Typically, with the collar 42 in its extended position, the needle can be inserted into the cap without interference from the collar. However, if necessary, the flexibility in the clip 38 can permit it to be flexed slightly so as to be out of the way. Once the needle is inserted into the cap, the clip 38 is drawn back toward the adaptor body 32 until the collar 42 partially circumferentially engages the septum cap 26. Because of the flexible nature of the rubber material of the septum cap, the collar can be snugly tightened against the cap, its position being maintained by the pawl-ratchet engagement. In other words, movement of the collar in the opposite, disengaging direction is prevented. When disconnection is desired, the collar 42 can be simply manually lifted or flexed away from the septum cap 26 and disengaged therefrom, permitting the needle 28 to be withdrawn from the cap. During use, the frictional engagement between the collar and the cap maintains the connection despite normal movement of the patient, thereby preventing accidental disengagement. The collar 42 can also be provided with burrs or prongs 43 in order to enhance this frictional engagement.

Figure 5:
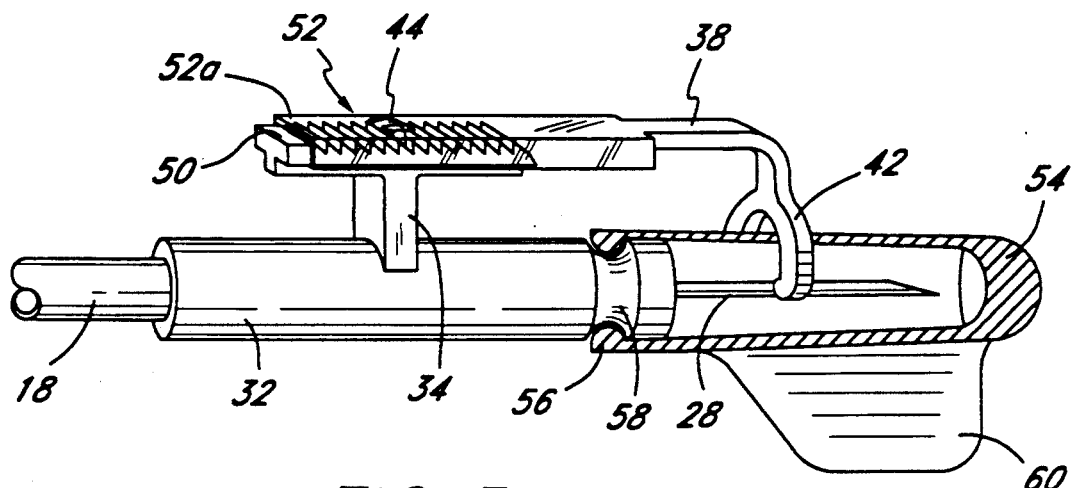
FIG. 5 is a perspective view of an alternate embodiment of the connector of the present invention illustrating a clip which is both slidable and rotatable, and also illustrating a needle cap.

FIG. 5 illustrates another embodiment of the present invention utilizing a clip 38 which is both slidable and rotatable. In this embodiment, the arm 34 extending radially from the adaptor body 32 supports a ratchet element 50 having a ratcheted surface formed thereon. The clip member, including a pawl 44, slidably engages the ratchet element 50 to form a rocker-type latch 52. The clip 38 is also provided with a collar 42 for engagement with the septum cap in a manner similar to that described above in connection with FIGS. 3 and 4. Thus, this combination of a slidable clip and a ratchet element forms a latch 52 which can be manually manipulated to move the collar 42 in a substantially radial or transverse direction (relative to the axis of the adaptor) away from or toward the septum cap. In other words, by manually depressing on the rear end 52a of the latch, the collar can be lifted so as to facilitate the sideport connection with the cap. When it is desired to secure the connection, the pressure on the rear end of the latch is released and the collar 42 resumes its normal position in approximate alignment with the axis of the adaptor body 32. The clip 38 is then slidably engaged with the septum cap in a manner similar to that described above in connection with FIGS. 3 and 4 and is securely retained in position by means of the ratchet and pawl assembly. If disconnection is desired, the rear end 52a of the latch 52 is simply depressed, thus raising the collar and permitting the needle to be removed from the septum.

This rotational movement of the latch 52 is very convenient since the septum cap usually does not present a smooth frusto-conical surface upon which the collar 42 can be slidably engaged. In other words, the collar may, in some instances, have to be lifted up by the latch 52 and placed down onto the cap (in order to clear, for example, a proximal ridge or lip on the cap) before slidable engagement can be completed.

FIG. 5 also illustrates a needle cap 54 for use in combination with the connector of the present invention whenever the connection is not engaged in the sideport. The needle cap 54 prevents accidental self-injection by completely surrounding the needle 28 as shown. Formed on the open mouth of the needle cap 54 is a lip or rim 56 which engages an annular groove 58 formed on the distal end of the adaptor body 32. The cap can be easily manually manipulated by a finger grip 60 extending radially away from the cap. The cap can be selectively placed on or removed from the present connector by means of a press-fit or interference fit in the annular groove 58.

Figure 6:
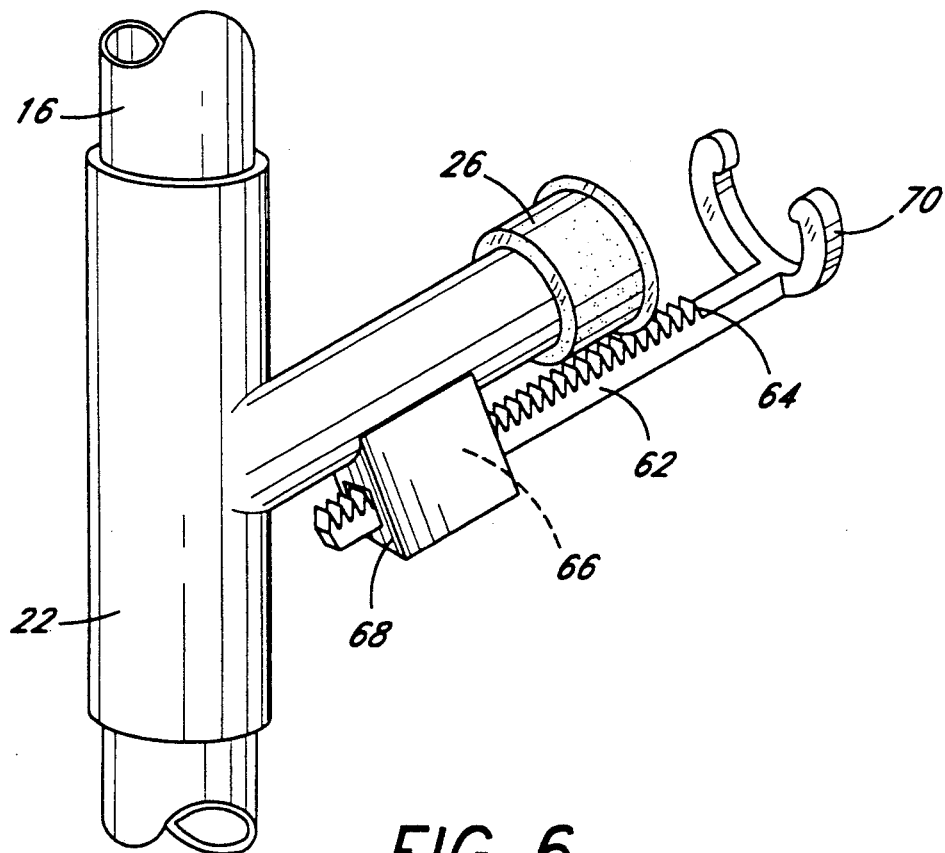
FIG. 6 is another embodiment of the present invention illustrating a clip mounted on the sideport member.

FIG. 6 illustrates another embodiment of the present invention in which a slidable clip mechanism 62 is mounted on the sideport 22. The clip 62 is provided with a ratcheted surface 64 similar to that described above which engages a pawl 66 supported in an arm 68 extending away from the sideport 22. The clip 62 is also provided with a collar 70 which engages the hub 72 of the IV needle 28 (FIG. 2) to be engaged in the septum connector. Thus, in this embodiment, a secure connection can be made at the sideport location with a standard IV tubing having a needle mounted on the distal end thereof.

While the preferred arrangement of the present invention has been illustrated and described, it should be understood that various changes and modifications to the system illustrated will readily come to mind which fall within the scope of the invention as set forth in the appended claims.

What is claimed is:

1. A sideport connector for removably connecting a first fluid supply tube to a second fluid supply tube, wherein said second fluid supply tube terminates in an end connector having a hub, said sideport connector comprising:

a sideport body defining at least a first and a second influent port, and at least one effluent port, said influent ports and said effluent port being in fluidic communication with one another, said first influent port being adapted to couple with the first fluid supply line and said second influent port being configured to engage the end connector of said second fluid supply line;

a housing connected to said sideport body;

a clip comprising a forward latch configured to engage the end connector hub of the second fluid supply tube, the clip being slidably connected to said housing to move in a direction generally parallel to the second fluid supply tube; and an interengaging element preventing said latch of said clip from moving away from said second effluent port.

2. A connector for removably connecting a first fluid supply tube to a port of a second supply tube, the port including a septum cap for receiving an intravenous needle, said connector comprising:

an adapter having a tubular body defined between a forward end and a rear end, said rear end being configured to receive an end of the first fluid supply tube;

an intravenous needle connected to said forward end of said tubular body, said intravenous needle communicating with an interior of said tubular body such that said tubular body communicates with the port of the second fluid supply tube with said intravenous needle inserted through the septum cap and into the port;

a support arm cantilevered radially outwardly from said adapter;

a clip comprising a forward latch configured to engage the septum cap, the clip slidably connected with said support arm to move in a direction parallel to a longitudinal axis of said adapter, said clip pivotably connecting to said adapter to move said forward latch radially outwardly away from said forward end of said adapter; and an interengaging element maintaining said clip from sliding away from said forward end of said adapter.

3. The connector of claim 2, wherein said support arm comprises a housing to which said clip is slidably engaged.

4. The connector of claim 3, wherein said interengaging element comprises a plurality of ratchet teeth positioned on said clip, and a pawl positioned in said housing of said support arm, said pawl being flexibly biased against and slidable over said teeth to permit said latch of said clip to slide towards said housing, said pawl cooperating with said teeth to prevent said latch from sliding away from said housing.

5. A connector for removably connecting a first fluid supply tube to a port of a second fluid supply tube, the port including a septum cap for receiving an intravenous needle, said connector comprising:
- an adapter having a tubular body defining an internal lumen defined between a forward end and a rear end, said rear end being configured to receive an end of the first fluid supply tube;
- an intravenous needle connected to said forward end of said tubular body, said intravenous needle communicating with said internal lumen;
- a housing connected to said adapter;
- a clip comprising a forward latch configured to engage the septum cap, said clip slidably connected to said housing to move in a direction parallel to a longitudinal axis of said internal lumen; and
- an interengaging element preventing said clip from sliding away from said forward end of said adapter.

6. The connector of claim 5, wherein said forward cap of said clip is adapted to frictionally engage the septum cap on the port in order to prevent disengagement of said adaptor from the port.

7. The connector of claim 5, wherein said interengaging element comprises a plurality of ratchet teeth positioned on said clip, and a pawl positioned in said housing, said pawl being flexibly biased against and slidable over said teeth to permit said latch of said clip to slide towards said housing, said pawl cooperating with said teeth to prevent said latch from sliding away from said housing.

8. The connector of claim 5, wherein said clip is flexible.

9. The connector of claim 5, further comprising a needle shield mounted on said adapter and partially surrounding said intravenous needle for preventing self-injection and contamination.

10. The connector of claim 9, wherein said needle shield has an elongated, generally semi-circular shape disposed about said intravenous needle with said needle shield attached to said adapter proximate to said forward end.

11. The connector of claim 5, further comprising a needle cap surrounding said needle and removably mounted on said adapter.

12. The connector of claim 11, wherein said adapter is provided with an annular groove and said needle cap comprises an open mouth which is press fit onto said groove of said adapter in order to selectively mount said cap on said adapter whereby the intravenous needle is protected.

13. The connector of claim 12, wherein said needle cap further comprises a finger grip.

14. A sideport connector for removably connecting a first fluid supply tube to a second fluid supply tube, the second fluid supply tube terminating in a hub at a distal end with an intravenous needle projecting from the hub opposite said second fluid supply tube, said sideport connector comprising:
- a sideport body defining at least a first and a second influent port, and at least one effluent port, said influent ports and effluent port being in fluidic communication with one another, said first influent port being adapted to couple with said first fluid supply line, said second influent port including a septum cap for receiving the intravenous needle of the second fluid supply line;
- a housing connected to said sideport body;
- a clip comprising a latch configured to engage the hub of the second fluid supply tube proximal of the needle, said clip being slidably connected to said housing to move in a direction generally parallel to the second fluid supply tube; and
- an interengaging element maintaining said clip in a manually selected position on said sideport body.

15. The sideport connector of claim 14, wherein said sideport body generally has a Y-shape.

16. The sideport connector of claim 14, wherein said interengaging element includes a plurality of ratchet teeth positioned on said clip and a pawl connected to said sideport body, said pawl being flexibly biased against and slidable over said teeth to permit said latch to slide towards said second influent port, said pawl cooperating with said teeth to prevent said latch from sliding away from said second influent port.

17. The sideport connector of claim 14, wherein said clip is flexible.

18. The sideport connector of claim 14, wherein said housing defines an aperture through which said clip extends, said clip being configured to slide through said aperture.

19. The sideport connector of claim 18, wherein said interengaging element includes a plurality of ratchet teeth positioned on said clip, and a pawl connected to said housing and positioned within said aperture, said pawl being flexibly biased against and slidable over said teeth to permit said latch of said latch to slide towards said housing, said pawl cooperating with said teeth to prevent said latch from sliding away from said housing.

* * * * *